(12) United States Patent
Reidt et al.

(10) Patent No.: US 9,632,078 B2
(45) Date of Patent: Apr. 25, 2017

(54) DETECTION OF ANTIGENS

(75) Inventors: Ulrich Reidt, Schwalmstadt (DE);
Alois Friedberger, Oberpframmem (DE); Christoph Heller, Taufkirchen (DE); Hero Brahms, Marburg (DE)

(73) Assignee: AIRBUS DEFENCE AND SPACE GMBH, Ottobrunn (DE)

( * ) Notice: Subject to any disclaimer, the term of this patent is extended or adjusted under 35 U.S.C. 154(b) by 212 days.

(21) Appl. No.: 13/383,167

(22) PCT Filed: Jul. 6, 2010

(86) PCT No.: PCT/EP2010/004128
§ 371 (c)(1),
(2), (4) Date: Mar. 23, 2012

(87) PCT Pub. No.: WO2011/003598
PCT Pub. Date: Jan. 13, 2011

(65) Prior Publication Data
US 2012/0171661 A1  Jul. 5, 2012

(30) Foreign Application Priority Data
Jul. 9, 2009 (DE) ......................... 10 2009 032 502

(51) Int. Cl.
G01N 33/549 (2006.01)
G01N 33/543 (2006.01)

(52) U.S. Cl.
CPC ............................... *G01N 33/54333* (2013.01)

(58) Field of Classification Search
None
See application file for complete search history.

(56) References Cited

U.S. PATENT DOCUMENTS

2008/0145869 A1* 6/2008 Ohzeki et al. .................. 435/7.9
2008/0193956 A1* 8/2008 Kricka et al. ...................... 435/8

FOREIGN PATENT DOCUMENTS

WO  2004057021 A2  7/2004

OTHER PUBLICATIONS

Fernandes CP et al. An immunomagnetic separation-PCR method for detection of pathogenic Leptospira in biological fluids. Hybridoma (Larchmt). Oct. 2008;27(5):381-6.*
KPL. New Product Information. Jun. 2008. http://www.kpl.com/catalog/productdetail.cfm?catalog_ID=17&Category_ID=456&Product_ID=548.*
KPL. 10% BSA Diluent/Blocking Solution. Publication date unknown. http://www.kpl.com/docs/datasheet/506110.pdf.*
Branen et al. Detection of *Escherichia coli* O157, *Salmonella enterica* Serovar Typhimurium, and Staphylococcal Enterotoxin B in a Single Sample Using Enzymatic Bio-Nanotransduction. Journal of Food Protection, vol. 70, No. 4, 2007, pp. 841-850.*
Xiao et al. Preparing a highly specific inert immunomolecular-magnetic beads for rapid detection and separation of *S. aureus* and group G *Streptococcus*. Appl Microbiol Biotechnol. Jul. 2007;75(5):1209-16. Epub Apr. 6, 2007.*
GenBank: M76178.1. Legionella pneumophila major outer membrane protein porin (omp28) gene, complete cds. Apr. 26, 1993. http://www.ncbi.nlm.nih.gov/nucleotide/149693?report=genbank&log$=nuclalign&blast_rank=11&RID=F7UWCRUF014.*
Sverre-Henning Brorson. Bovine serum albumin (BSA) as a reagent against non-specific immunogold labeling on LR-White and epoxy resin. Micron vol. 28, No. 3, pp. 189 195, 1997.*
Tamás Arányi et al. The BiSearch web server, BMC Bioinformatics 2006, 7:431 doi:10.1186/1471-2105-7-431.*
Catalan et al. Detection of Legionella pneumophila in wastewater by nested polymerase chain reaction. Res Microbiol. Jan. 1997;148(1):71-8.*
Amagliani et al. Development of a magnetic capture hybridization-PCR assay for Listeria monocytogenes direct detection in milk samples. Journal of Applied Microbiology 100 (2006) 375-383.*
Whiteaker et al. Antibody-based enrichment of peptides on magnetic beads for mass spectrometry-based quantification of serum biomarkers. Anal Biochem. Mar. 1, 2007; 362(1): 44-54.*
Safarik et al. J. Appl. Bacteriol. 1995, 78, 575-585.*
Streptavidin Microbeads. Miltenyi Biotec. 2006. https://www.miltenyibiotec.com/~/media/Images/Products/Import/0001200/IM0001276.ashx.*
Hoffman, et al., Cloning and Nucleotide Sequence of a Gene (ompS) Encoding the Major Outer membrane Protein of Legionella pneumophila; Journal of Bacteriology, 174:914-920 (1992).
Engelhart, et al., Hospital-acquired legionellosis originating from a cooling tower during a period of thermal inversion; International Journal of Hygiene and Environmental Health; 211:235-240 (2008).
Poustka, et al., Generation Annotation, Evolutionary Analysis, and Database Integration of 20,000 Unique Sea urchin EST Clusters; Genome Research; 13:2736-2716 (2003) and Databse EMBL [Online].
Dias Neto, et al., Shotgun sequencing of the human transcriptome with ORF expressed sequence tags; PNAS; 97:3491-3496 (2000).
Aoyama, et al, The actin-related protein hArp8 accumulates on the mitotic chromosomes and functions in chromosome alignment; Experimental Cell Research; 314:859-868 (2008).
International Bureau, International Search Report for PCT/EP2010/004128 dated Dec. 21, 2010, pp. 1-6.
Yu, et al., "Detection of biological threat agents by immunomagnetic microsphere-based solid phase fluorogenic and electro-chemiluminescence", Biosensors & Bioelectronics, 14:829-840 (2000).
Yanez, et al., "Quantitative Detection of Legionella pneumophila in Water Samples by Immunomagnetic Purification and Real-Time PCR Amplificatio of the dotA Gene", Applied and Environmental Microbiology, 71:3233-3441 (2005).

(Continued)

*Primary Examiner* — Nick Zou
(74) *Attorney, Agent, or Firm* — McAndrews, Held & Malloy, Ltd.

(57) ABSTRACT

The invention discloses a method for detecting at least one antigen, comprising the following steps: providing magnetic beads, which are coated with antibodies specific for at least one antigen to be detected; bringing the magnetic beads in contact with a washing buffer that comprises at least 8% BSA and incubating the mixture with a sample; isolating the magnetic beads by means of magnetic separator; and detecting the antigens bound to the magnetic beads by the antibodies. Washing buffers, primers, kits and devices that can be used for said methods are also disclosed.

14 Claims, 3 Drawing Sheets

(56) References Cited

OTHER PUBLICATIONS

Western Blotting Handbook and Troubleshooting Guide.
Aoyama, et al., "The actin-related protein hArp8 accumulates on the mitotic chromosomes and functions in chromosome alignment", Experimental Cell Research, 4:859-868 (2008).
Engelhart, et al., "Hospital-acquired legionellosis originating from a cooling tower during a period of thermal inversion", Int. J. Hyg. Environ-Health, 211:235-240 (2008).
Lundqvist, et al., "Nanoparticle size and surface properties determine the protein corona with possible implications for biological impacts", PNAS, 105:14265-14270 (2008).
Chang, et al, "Analysis of Peptides and Proteins Affinity-Bound to iron Oxide Nanoparticles by MALDI MS", J. American Society Mass Spectrometry, 18:910-918 (2007).
Brewer, et al., Probing BSA Binding to Citrate-Coated Gold Nanoparticles and Surfaces, Langmuir, 21:9303-9307 (2007).
Bollag et al., "Immunoblotting", Protein Methods, 2nd Ed., Chapter 8:195-227 (1996).
Cedervall, et al., "Understanding the nanoparticle-protein corona using methods to quantify exchange rates and affinities of proteins for nanoparticles", PNAS, 104:2050-2055 (2007).
Chithrani, et al., "Determinnig the Size and Shape Dependence of Gold Nanoparticle Uptake into Mammalian Cells", Nano Letters, 6:662-668 (2008).
Glomm, et al., "Adsorption Behavior of Acidic and Basic Proteins onto Citrate-Coated Au Surfaces Correlated to Their native Fold, Stability, and pI", J. Phys. Chem., 111:14329-14345 (2007).
Silin, et al., "SPR Studies of the Nonspecific Adsorption Kinetics of Human IgG and GSA on Gold Surfaces Modified by Self-Assembled Monolayers (SAMs)", Journal of Colloid and Interface Science, 185:94-103 (1997).
Lindman, et al., "Systematic Investigation of the Thermodynamics of HSA Adsorption to N-iso-Propylacrylamide/N-tert-Butylacrylamide Copolymer Nanoparticles. Effects of Particle Size and Hydrophobicity", Nano Letters, 7:914-920 (2007).
Ashwinkumar A. Bhirde, et al., Role of Albumin in the Formation and Stabilization of Nanoparticle Aggregates in Serum Studied by Continuous Photon Correlation Spectroscopy and Multiscale Computer Simulations, The Journal of Physical Chemistry, Jun. 30, 2014, pp. 16199-16208, Besthesda, MD, US.
Geoffrey J. Brownsey, et al., The Glass Transition Behavior of the Globular Protein Bovine Serum Albumin, Biophysical Journal, vol. 85, Dec. 2003, pp. 3943-3950, Colney, Norwich, UK.
Shinya Ikeda, et al., Intermolecular Forces in Bovine Serum Albumin Solutions Exhibiting Solidlike Mechanical Behaviors, Aug. 28, 2000, pp. 757-763, Osaka, Japan.

\* cited by examiner

DETECTION OF ANTIGENS

CROSS-REFERENCE TO RELATED APPLICATIONS

This application is a U.S. National Phase of International Application No. PCT/EP2010/004128, filed Jul. 6, 2010, which claims priority from German Patent Application No. 102009032502.6 filed Jul. 9, 2009, which are incorporated herein by reference in their entirety.

FIELD OF INVENTION

The present invention relates to the field of detection of pathogens and toxins in samples by the use of magnetic beads coated with antibodies.

BACKGROUND OF THE INVENTION

The detection of pathogens or toxins in samples is highly relevant, e.g. for clinical or security applications. Thus it is often desirable to be able to detect a certain pathogen and/or toxin in a sample within a short period of time.

A plurality of detection methods based on the use of antibodies directed against the pathogen and/or toxin are known in the state of the art. Antibodies are therefore often used since they generally display a high binding constant for their antigen and thus achieve a high specificity. Furthermore, antibodies can be generated for almost any number of antigens, i.e. e.g. pathogens or toxins.

Nevertheless, a cross-reactivity is always problematic in the use of antibodies, i.e. an unspecific binding to undesired targets. Accordingly, in the use of antibody-based detection methods also binding reactions of the antibodies to molecules not corresponding to the actual antigens of the antibodies always occur. Thus, the detection of so-called false positive antigens often takes place. Moreover, a binding to the substrate is often observed of antigens not corresponding to the antigens to be detected, however which are detected by the subsequent detection method. For example, on contacting antibody-coated magnetic beads with a sample, antigens found in the sample, like e.g. phylogenetically related pathogens, also always bind to the beads themselves and not to the antibodies bound thereto. In the subsequent detection reaction these antigens, which are actually not to be detected, then are in part also identified as false positives, or as "background" hamper the detection of the antigens really to be detected.

SUMMARY OF THE INVENTION

The function of the present invention is to provide a highly specific and reliable antibody-based detection method for the detection of pathogens and/or toxins. A further function of the present invention consists in providing a particular washing buffer which can be employed in said method, specific primer sequences for the detection of certain pathogens, as well as kits and devices for performing the method of the invention. Concerning the detection method, the problem is solved by the method of claim 1. Particularly, a method for the detection of at least one antigen is provided, comprising the steps of: a) providing magnetic beads coated with antibodies specific for at least one antigen to be detected; b) contacting the magnetic beads with a washing buffer comprising at least 8% BSA; c) incubating the mixture of step b) with a sample; d) isolating the magnetic beads using a magnetic separator; and e) detecting the antigens bound to the magnetic beads via the antibodies.

Concerning the washing buffer, the primer sequences, the kits and devices the problem is solved according to claims 8, 9, 10, and 11, respectively.

The present invention is based on the surprising finding that the use of a washing buffer comprising at least 8%, and preferably 10%, BSA enables the highly specific binding to their antigens of the antibodies employed, i.e. the significantly reduces both the number of false positives as well as the background reaction.

The method of the present invention is based on antibody-coated magnetic beads as a central element. Magnetic beads, designated briefly as "beads" in the following, are known to the skilled person and can be obtained for example from Invitrogen. Usually, they consist of small polymer spheres, preferably consisting of latex and/or polystyrene, having a paramagnetic core. The beads themselves preferably have a diameter in the range of about 1 μm to 50 μm. The skilled person, however, will realise that any other suitable material and/or other sizes of the beads can be employed.

The coating of the beads with antibodies is also called "coating" and can be effected with several methods sufficiently known to the skilled person. Preferred methods for coating the beads with antibodies include: a) passive adsorption, e.g. via hydrophobic interactions; b) direct chemical coupling, also known as "cross-linking", preferably via a peptide bond or other bonds; c) coupling via immobilised antibody-binding proteins, like for example protein A; d) coupling via a biotin-streptavidin bond.

In a preferred embodiment, the coating is effected using a biotin-streptavidin bond, which exploits the high affinity of two particular biological molecules to each other, namely biotin and streptavidin. For this, the antibody is labelled with the molecule biotin on the side facing away from the specific binding sites, the so-called Fc domain. Concomitantly, the protein streptavidin is coupled to the surface of the beads. When the antibodies and beads are now mixed, the antibodies are favourably virtually irreversibly bound to the sphere surface.

A further advantage of this embodiment consists in the fact that only a single type of beads, namely streptavidin beads, has to be produced. By coupling with biotinylated antibodies, beads with nearly any desired specificity can thus be simply generated.

After immobilisation of the antibodies on the beads, these can be employed for the targeted "capture" of the specific antigens, i.e. e.g. of pathogens and/or toxins.

The antibodies can be directed against any antigens. In one embodiment of the invention, the antibodies are directed against antigens selected from the group consisting of pathogens, toxins, micro-organisms, bacteria, viruses, fungi, bacterial spores, fungal spores, protozoa like anthrax, biological toxins like ricin, abrin, LPS, or other substances of non-biological origin, e.g. explosives or drugs. In preferred embodiments, the antibodies are directed against *Legionella*, adenoviruses, or the bacterium *E. coli*. Even more preferably, the antibodies are directed against *Legionella pneumophila* or against Adenovirus subgroup C, serotype 6. In further preferred embodiments the antibodies are directed against particular surface structures of the antigens.

The antibodies of the present invention can either be provided by the skilled person using sufficiently known methods, for example using the hybridoma technology, or be obtained commercially, for example from Acris Antibodies, Novus Biologicals, and/or Abcam.

In one embodiment the antibody is a polyclonal antibody, preferably it is a monoclonal antibody. This has the advantage of achieving a higher specificity.

An antibody is regarded as a "specific antibody" herein if it exhibits a sufficiently high binding constant for its antigen so as to enable the detection of the antigen using the methods of the present invention. This means that the binding constant must be sufficiently high to complex the target molecule. In preferred embodiments, such a specific antibody has a binding constant of about $10^5 M^{-1}$ to about $10^{10} M^{-1}$, preferably $10^8 M^{-1}$ to about $10^{11} M^{-1}$, more preferably $10^9 M^{-1}$ to about $10^{12} M^{-1}$. A higher binding constant of an antibody has the advantage that the corresponding antigen can be detected with higher specificity and with shorter incubation time.

In a preferred embodiment, the beads comprise more than one specific antibody. This means that either different types of beads having one antibody each and/or one type of beads having at least two antibodies each are provided. In a more preferred embodiment, antibodies for a micro-organism, i.e. a bacterium, virus, and/or fungus, are provided, along with antibodies for a toxin produced by this micro-organism. This has the advantage of achieving an improved specificity and/or sensitivity on detection, since in addition to the micro-organism to be detected, a toxin produced by it is also always detected.

While in most conventional detection methods the capture antibodies are bound to a solid matrix, e.g. microtiter plates, membranes, or columns, the use of magnetic beads according to the invention provides greater flexibility and renders the assay largely independent of a particular format or a particular platform.

In a further step of the method of the invention, the beads are contacted with a washing buffer. For this contacting of the beads, any suitable vessel type, e.g. microtiter plate, column, microchannels, etc., can be used.

According to the invention, the beads are thereby contacted with a washing buffer comprising at least 8% BSA, i.e. bovine serum albumin. Preferably the washing buffer comprises $\geq 8\%$ and $\leq 12\%$ BSA, more preferably the washing buffer comprises $\geq 9\%$ and $\leq 10\%$ BSA, most preferably the washing buffer comprises a BSA content of 10%. Surprisingly, it was found that such concentrations of BSA permit an excellent and significantly better detection of the antigens. The percentage values refer to weight percent. In a further preferred embodiment, the BSA is a biotin-free BSA.

In further preferred embodiments, the washing buffer further comprises at least one detergent and water, preferably aqua dest., for filling up. In a further preferred embodiment, the detergent is Tween 20 and/or Triton X and is more preferably present at a concentration of 0.01 vol.-%.

In further preferred embodiments, the washing buffer comprises at least one of the following substances: potassium chloride, potassium dihydrogen phosphate, disodium hydrogen phosphate, and/or sodium chloride. More preferably, these substances are present at the following concentrations: potassium chloride 2.7 mM, potassium dihydrogen phosphate 1.5 mM, disodium hydrogen phosphate 8.1 mM, and/or sodium chloride 136.9 mM.

In a further preferred embodiment, the washing buffer is a PBS washing buffer comprising potassium chloride, potassium dihydrogen phosphate, disodium hydrogen phosphate, and/or sodium chloride and further comprises BSA and preferably at least one detergent.

In a further preferred embodiment, the washing buffer has a pH of $\geq 5$ and $\leq 9$, more preferably $\geq 6$ and $\leq 8$, even more preferably $\geq 6.5$ and $\leq 8$ or $\geq 7$ and $\leq 8$, most preferably of about 7.4. In a further embodiment, said pH value of the washing buffer is adjusted using HCl or NaOH.

In a further preferred embodiment, the beads are incubated with the washing buffer for a certain period of time. Preferably this period of time extends from $\geq 1$ min and $\leq 24$ h, $\geq 30$ min and $\leq 12$ h, $\geq 1$ h and $\leq 6$ h, $\geq 2$ h and $\leq 8$ h. More preferably, the incubation is carried out overnight.

In a further step of the method of the invention the beads contacted with washing buffer are incubated with a sample. For this incubation, again any suitable vessel type can be used, e.g. microtiter plate, column, microchannels, etc.

The sample can be any suitable sample that could contain an antigen to be detected. In preferred embodiments, the sample is a fluid, semifluid or gaseous sample, a body fluid, blood, saliva, serum, tear fluid, urine, a food sample, a swab, e.g. from a critical area or building like a courthouse, a hospital, a war zone or from space. In further embodiments, the sample is derived from a ventilation system, for example an air conditioner, more preferably from the ventilation system of a hospital, of a public facility, or of an airport.

The incubation occurs by contacting the beads contacted with washing buffer with the sample under conditions suitable for permitting complexing of the at least one specific antibody on the beads with its antigen. In preferred embodiments, the incubation is carried out at room temperature or at a temperature between $\geq 20°$ C. and $\leq 40°$ C., $\geq 30°$ C. and $\leq 40°$ C., and more preferably at about 37° C.

In a further preferred embodiment, the incubation occurs over a period of time of $\geq 1$ min and $\leq 3$ h, $\geq 10$ min and $\leq 2$ h, $\geq 20$ min and $\leq 2$ h, $\geq 45$ min and $\leq 1.5$ h. More preferably, the incubation occurs over a period of time of about 1 h.

In a further preferred embodiment, the incubation occurs under slight continuous or discontinuous stirring of the mixture, for example by swinging, shaking, churning, and the like. Even more preferably, the stirring occurs every 5, 10, 15, 30, or 45 min, more preferably every 15 min of the incubation time.

In a preferred embodiment of the invention, the incubation step is followed by at least one washing step, more preferably by $\geq 2$, $\geq 3$, $\geq 4$, or $\geq 5$ washing steps. This has the advantage of removing unspecific antigens from the beads and thus increasing the specificity and/or sensitivity of the method.

In a further preferred embodiment, the at least one washing step occurs on a magnetic separator, i.e. in the proximity of a magnet retaining the paramagnetic beads. This has the advantage that none of the beads are lost during the at least one washing step.

In an especially preferred embodiment, for at least one of the at least one washing step the same washing buffer is used as for the contacting of the beads at the beginning of the method of the invention. Most preferably, the identical washing buffer of the invention used for the contacting of the beads is used for all washing steps. It has been found that the washing buffer of the invention is suitable especially for the washing of the incubated beads and leads to a higher sensitivity and specificity of the detection method of the invention. A further advantage is that only a single washing buffer has to be provided for the method of the invention, leading to a saving of time and costs as well as of space in the kit of the invention.

In a further step of the method of the invention, the magnetic beads are separated using a magnetic separator. For this a magnet, i.e. the magnetic separator, is brought near the paramagnetic beads, retaining these, and the supernatant of the suspension is subsequently discarded. If, for example, the beads were situated in a vessel for the incubation, the magnetic separator is brought near the vessel from the outside, whereby the beads adsorb to the inner wall of the vessel and are retained there. Afterwards, the fluid contained in the vessel, i.e. substantially the washing buffer and the sample, can be poured out, whereby the beads remain in the vessel and have thus been isolated. If the washing step described above has been performed after the incubation and such a separator has been used, the beads are already adsorbed to e.g. the vessel wall and only the washing buffer has to be discarded for the isolation.

In a further step of the method of the invention, a detection of the antigens bound to the isolated beads via the antibodies is carried out. Such a detection will advantageously exhibit a significantly improved specificity and/or sensitivity, i.e. ultimately an improved detection limit, thereby enabling, apart from a higher accuracy and reliability of the detection, also a saving of time, i.e. a detection to be carried out faster. This is made possible by the fact that an improved, i.e. more specific, isolation of the antigens via the beads is achieved by the employed washing buffer of the invention.

The detection of the antigens bound to the isolated beads can be performed according to any method known to the skilled person. In preferred embodiments, this detection occurs immunologically and/or using a nucleic acid amplification method. A nucleic acid amplification method requires that the antigen comprise a nucleic acid, this is the case for example with micro-organisms like bacteria, viruses, protozoa and or fungi.

In the following, two particular ones of the preferred detection methods of the immunological and the nucleic acid amplification method, respectively, shall be detailed.

A preferred immunological detection method according to the invention is the enzyme-linked immunosorbent assay (ELISA), more preferably the Sandwich ELISA. ELISA is a method well known to the skilled person for detecting certain molecules, i.e. antigens, in a targeted manner. For this, the mechanisms of the immune system are used: If a substance is recognised as foreign by the immune system, it forms antibodies that dock to the foreign molecule, thus labelling it. This so-called antibody-antigen interaction is used for the ELISA assay. If a certain antigen is to be detected, the appropriate antibodies have to be known and must have been produced using different genetical or cell biological methods. If then the sought molecule is present in a sample, it is bound to an antibody—which has previously been applied to a carrier medium—and thereby isolated out of the sample ("captured"). The antibody-coated beads of the present invention correspond to said carrier medium with the antibodies bound thereto.

In the Sandwich ELISA, to the antigens thus immobilised a second antibody is bound which can be detected or is used for the generation of a detectable signal, respectively. This means that during immunological detection according to the present invention a second, i.e. so-called secondary, antibody for the antigen is used.

Different ways are known to the skilled person for generating a detectable signal using said second antibody. In a preferred embodiment, the second antibody is coupled to an enzyme, a so-called conjugate, the help of which the detectable signal is generated with. In a further preferred embodiment this can take place via conversion of a substrate and light emission and/or colour production generated thereby. In an especially preferred embodiment, the secondary antibody is coupled to the enzyme "horseradish peroxidase" (HRP). A reaction catalysed by this enzyme, in which 3,3',5,5'-tetramethylbenzidine (TMB) is converted, then leads to a visible colour precipitate which can be evaluated subsequently with special analysis instruments. Conjugated antibodies can be obtained for example from the above-mentioned producers.

In a preferred embodiment of the invention the detection of the antigens coupled to the beads via the antibodies therefore occurs immunologically via a Sandwich ELISA.

For this, the method of the invention further comprises the step of taking up the beads isolated with the magnetic separator in a conjugate solution, followed by the incubation of the beads in said conjugate solution.

In a preferred embodiment the conjugate solution contains a secondary antibody specific for the antigen and present conjugated to an enzyme. More preferably, the enzyme is capable of catalysing a light or colour reaction. Most preferably the enzyme is HRP. In a further embodiment the conjugate buffer comprises PBS, in which the secondary antibody is diluted, preferably the secondary antibody is present at a concentration of 1:500, 1:750, 1:1000, or 1:1500.

The incubation occurs by contacting the isolated beads with the conjugate solution under suitable conditions allowing a complexing of the conjugated, secondary antibody with its antigen, which is present immobilised on the antibodies of the beads. In preferred embodiments, the incubation is carried out at room temperature or at a temperature between $\geq 20°$ C. and $\leq 40°$ C., $\geq 30°$ C. and $\leq 40°$ C., and more preferably at about 37° C.

In a further preferred embodiment, the incubation occurs over a period of time of $\geq 1$ min and $\leq 3$ h, $\geq 10$ min and $\leq 2$ h, $\geq 20$ min and $\leq 2$ h, $\geq 45$ min and $\leq 1.5$ h. More preferably, the incubation occurs over a period of time of about 1 h.

In a further preferred embodiment, the incubation occurs under slight continuous or discontinuous stirring of the mixture, for example by swinging, shaking, churning, and the like. Even more preferably, the stirring occurs every 5, 10, 15, 30, or 45 min, more preferably every 15 min of the incubation time.

In a preferred embodiment of the invention, the incubation step is followed by at least one washing step, more preferably by $\geq 2$, $\geq 3$, $\geq 4$, or $\geq 5$ washing steps. This has the advantage of removing unspecific antigens from the beads and thus increasing the specificity and/or sensitivity of the method. Preferably PBS is used for the washing step.

In a further preferred embodiment, the at least one washing step occurs on a magnetic separator, i.e. in the proximity of a magnet retaining the paramagnetic beads. This has the advantage that none of the beads are lost during the at least one washing step.

In a further embodiment, the method of the invention further comprises contacting the washed beads isolated with the magnetic separator with an HRP solution and a TMB substrate solution. In a preferred embodiment, the HRP solution comprises potassium citrate, more preferably at a concentration of 30 mM in aqua dest. and has been adjusted to a pH value of approximately 4.1. For this, KHO is advantageously used. In a further preferred embodiment, the TMB substrate solution comprises, additionally to TMB preferably at a concentration of 10 mM, acetone, ethanol, and hydrogen peroxide.

After stirring of the mixture of isolated beads, HRP solution, and TMB substrate solution, another incubation step occurs according to the invention. In preferred embodiments, the incubation is performed at a temperature between $\geq 20°$ C. and $\leq 40°$ C., $\geq 30°$ C. and $\leq 40°$ C., or more preferably at room temperature.

In a further preferred embodiment, the incubation occurs over a period of time of ≥1 min and ≤2 h, ≥10 min and ≤1.5 h, ≥20 min and ≤1 h, ≥30 min and ≤1 h. More preferably, the incubation occurs over a period of time of about 45 min.

After the incubation has occurred, a stopping of the reaction occurs by addition of a stopping solution, preferably comprising 1 M $H_2SO_4$. In a preferred embodiment, the mixture is briefly stirred afterwards and/or again incubated at a temperature between ≥20° C. and ≤40° C., ≥30° C. and ≤40° C., or more preferably at room temperature. The incubation occurs advantageously over a period of time of ≥1 min and ≤20 min, ≥5 min and ≤15 min, and more preferably over a period of time of about 10 min.

In a further step of the method of the invention, a photometric or colorimetric evaluation then occurs, using an evaluation instrument sufficiently known to the skilled person.

As described further above, in another embodiment of the invention the detection can also occur using a nucleic acid amplification method. As also mentioned, this requires that the "antigen" comprise i.e. a nucleic acid. In the following, an "antigen" will always be talked of even if this term is actually borrowed from immunology. Yet it will be understood by the skilled person that certain "substances" detectable by the method of the invention may both be an antigen as well as comprise a nucleic acid. These comprise e.g. the micro-organisms, bacteria, viruses, and fungi.

A plurality of nucleic acid amplification methods is known to the skilled person. All such methods rely substantially on the enzymatic amplification of a nucleic acid of an antigen, thereby enabling a subsequent detection of the amplified nucleic acid. Apart from the enzyme, so-called "primers" and nucleotides are necessary for such an amplification. The skilled person is familiar with further buffers and substances.

The term "nucleic acid" as used herein denotes a ribonucleic acid, preferably a deoxyribonucleic acid. This can be of natural origin, i.e. have been derived i.a. from organisms, tissue, cells, or bioplate. In a preferred embodiment, the nucleic acid is a DNA (deoxyribonucleic acid), a cDNA, more preferably a genomic DNA. The nucleic acid can be provided in single-stranded, double-stranded or multi-stranded form.

The term "amplification" as used herein denotes the multiplication of a nucleic acid (template or matrix nucleic acid) by a factor of at least 2. Preferred methods for the amplification of nucleic acids are global amplification methods, which amplify the total transformed nucleic acid in a sample. These include isothermal and non-isothermal whole genome amplification (WGA) methods. Examples for amplification methods are RCA (rolling circle amplification) and MDA (multiple displacement amplification). The skilled person is familiar with further linear and exponential amplification methods suitable for the present invention, inter alia PCR (polymerase chain reaction), LCR (ligase chain reaction), NASBA (nucleic acid sequence based amplification), SDA (strand displacement amplification), TMA (transcription mediated amplification), 3SR (self-sustained sequence replication), LAMP (loop-mediated amplification), HDA (helicase dependent amplification), RPA (recombinase-polymerase amplification).

An especially preferred nucleic acid amplification method for the purposes of the invention is PCR. PCR is a method by means of which minimal amounts of a DNA section can be multiplied (amplification) in a chain reaction. PCR is very frequently employed nowadays if proofs are to be provided by means of certain DNA sequences, such as in criminalistics/forensics or in a paternity test, in microbiology for the detection of living and dead bacteria (total cell number), in medical diagnostics, when virus DNA is to be detected in blood or other body fluids, in evolutionary biology for tracing family relationships and lines of descent, and/or in food analysis for detecting the presence of components from genetically modified organisms (GMO).

In order to be able to perform a PCR detection, two short pieces of DNA (primers) fitting to the sought DNA strand have to be provided. The chain reaction started by them runs through several cycles in each of which the DNA amount is doubled by a polymerase.

The term "primer" as used herein denotes a molecule that serves as a starting point for an enzyme with nucleic acid polymerase or nucleic acid ligase activity. A primer can be a protein, a nucleic acid, or another molecule, which to the skilled person proves to be a polymerase or ligase starting point. Said molecule can serve as a starting point by means of intermolecular, but also intramolecular, interaction. Preferably the primers are nucleic acid primers. These can hybridise with the template nucleic acid over their whole length or display partial mismatches and usually have a length of 4 to 100 nucleotides (nt). The length of the primers preferably ranges between 5 and 50 nt, and especially preferably between 6 and 25 nt.

The term "primer set" as used herein denotes a host of primers required for performing an amplification and consists of at least one primer. For linear amplifications, a primer set consists of at least one primer. For exponential amplification, too, a primer set consists of at least one primer, if the latter hybridises at least two different positions of the template nucleic acid, whereby the nucleic acid section located between the hybridisation positions is amplified exponentially. Preferably, however, for exponential amplifications the primer set consists of at least two primers hybridising at two different positions of the template nucleic acid; here also, the nucleic acid section located between the hybridisation positions is amplified exponentially.

The term "polymerase" as used herein denotes an enzyme catalysing the formation of phosphodiester bonds between individual nucleotides within a nucleic acid strand (e.g. DNA and RNA polymerases). Especially preferred for use in the method for amplification of the invention are polymerases suitable for amplification reaction, in particular all DNA polymerases. The polymerases can be differentiated into heat-labile or heat-stable enzymes. Not all polymerases are suited equally well for different amplification methods. Thus, polymerases with strand displacement activity are suitable for isothermal amplification methods, while heat-stable polymerases are preferred for non-isothermal amplification methods. Preferred polymerases include polymerases with enzyme number EC 2.7.7.7, Taq polymerase, polymerases with proofreading activity, polymerases with strand displacement activity, mutated polymerase, as well as polymerases with accessory factors (e.g. helicase, single strand binding proteins, recombination proteins) and holoenzymes forming a functional DNA-polymerase complex.

In a preferred embodiment, the polymerase is a DNA polymerase, more preferably a Taq polymerase, a polymerase with proofreading activity, or a polymerase with strand displacement activity. A strand displacement activity is a property of a polymerase by means of which a peeling off of the "old" strand ("strand displacement") of a double-stranded nucleic acid from the other "old" strand is effected during a polymerase reaction. Belonging to the strand displacement polymerases are all polymerases able to perform a strand displacement. These include enzymes, like e.g.

Phi29 DNA polymerase, Klenow exominus DNA polymerase, Vent DNA polymerase, Deep Vent™ DNA polymerase, Bst DNA polymerase, 9oNm™ DNA polymerase, and Bca DNA polymerase.

The strand displacement polymerases can also be provided in mutated form, e.g. as so-called exominus variants (i.e. without exonuclease activity). These include polymerase like the Phi29 DNA polymerase, Klenow exominus DNA polymerase. Furthermore, further accessory factors improving or enabling the amplification of the nucleic acid transformed by bisulphitation can be added to the polymerase. These factors include e.g. helicases, single strand DNA binding proteins (e.g. SSB, T4gp32), recombination proteins (e.g. recA, Mut proteins).

The term "ligase" as used herein denotes a ligase linking (ligating) two nucleic acid strands by generating a phosphorester bond. These include DNA as well as RNA ligases. Thus "ligase" denotes an enzyme with the enzyme number EC 6.5.1.1, EC 6.5.1.2, and EC 6.5.1.3, respectively.

In a preferred embodiment of the invention the detection of the antigens bound to the beads via the antibodies therefore occurs using a nucleic acid amplification method. In an especially preferred embodiment, the nucleic acid amplification method is a PCR.

For this the method of the invention further comprises the step of taking up at least a part of the beads isolated using the magnetic separator into a nucleic acid amplification mixture.

In a preferred embodiment, the nucleic acid amplification mixture comprises Tris-HCl, preferably at a pH of 8.3, KCl, MgCl$_2$, a nucleotide mix of the four nucleotides dATP, dTTP, dGTP, and dCTP, as well as an amplification enzyme. More preferably the nucleic acid amplification mixture is a PCR reaction mixture and comprises 10 mM Tris-HCl, preferably at a pH of 8.3, 50 mM KCl, 1.5 mM MgCl$_2$, a nucleotide mix of the four nucleotides dATP, dTTP, dGTP, and dCTP with a concentration of 200 μM each, as well as Taq DNA polymerase, preferably at a concentration of 0.02 U.

The nucleic acid amplification mixture further comprises a primer specific for the antigen, preferably a primer pair specific for the antigen. A primer or primer pair is considered specific for a particular antigen if it hybridises with the nucleic acid of the antigen under high salt conditions. Preferably a specific primer or specific primer pair exhibits a complete sequence identity to the nucleic acid of the antigen to be detected. In a further preferred embodiment 100 pmol of each primer are used per reaction mixture.

In especially preferred embodiments, the antigen to be detected is *Legionella pneumophila* and the primer and/or the primer pair is specific for the ompS gene of *Legionella pneumophila*. The marker gene ompS is a highly conservative gene coding for a membrane protein. The term "highly conservative" means that this marker gene is suitable for the detection of different serogroups (*Legionella* serogroup 1-12). This marker gene has previously never been used in a fast and sensitive assay. In the present invention the ompS gene is used for the first time for the detection of *Legionella pneumophila*. In an especially preferred embodiment, the primer pair with the following sequence is employed: ompS_Leg_forward 5'-GCG GCT GTA TTT GCT CTG GGA A-3' (SEQ ID NO: 1) and ompS_Leg_reverse 5'-TAA GCC TAT GTA GGG GCC AGA TGC-3' (SEQ ID NO: 2).

In further especially preferred embodiments, the antigen to be detected is an adenovirus and the primer and/or primer pair is specific for the adenoviral hexon gene. The hexon marker gene also codes for a surface protein and, in contrast to the ompS gene, is used routinely in diagnostics. Due to a very high mutation rate, the sequence of the gene is subject to continual change. Highly conservative regions over several serogroups are therefore very rare. By intensive research, however, the identification of two previously unknown such regions has succeeded. In these regions highly specific hexon primers have been designed enabling a fast and very sensitive detection. These regions have previously never been used in a detection and the sequence of the detection primers is disclosed in this invention for the first time. In an especially preferred embodiment, the primer pair with the following sequence is employed: hexon_AdV_forward 5'-GAA ATG ACA CCA ACG ACC AG-3' (SEQ ID NO: 3) and hexon_AdV-reverse 5'-GGG AAC ATT AGC GGG GTA AG-3' (SEQ ID NO: 4).

In a further step of the method of the invention, at least one round of amplification now occurs. The manner in which such a round of amplification is performed depends on both the amplification enzyme used as well as on the amplification method employed.

In the preferred PCR amplification method amplification occurs in several cycles, preferably ≥20, ≥25, ≥30, or ≥35 cycles, with three reaction steps each. In the first reaction step the DNA double strand is melted into single strands by heating. This preferably occurs at about 95° C. In a second step, the temperature is lowered for annealing the primers. The respective optimal annealing temperature depends on the length and the sequence of the primer used and can be calculated without problems by the skilled person. In the third reaction step, starting from the primers, double strands are synthesised ("elongation") in the presence of the nucleotides (dNTPs), to which end the temperature is increased to the optimal reaction temperature of the polymerase, in the case of the Taq polymerase to 72° C. The elongation time depends on the length of the fragment to be amplified and can also be calculated by the skilled person. Generally, an elongation time of 1 min per 1 kb of nucleic acid to be amplified is assumed. The resulting DNA double strands on their part serve as matrices in the next cycle, resulting in an exponential amplification of the DNA fragment.

For example, the PCR amplification can occur under the following conditions: 1) denaturation: 95° C. for 5 min, 2) denaturation: 95° C. for 20 s, 3) annealing of the primers: for *Legionella pneumophila* at 58° C., for adenovirus at 54° C. for 20 s, 4) synthesis, i.e. elongation at 72° C. for one minute. Steps 2) to 4) are repeated for 30-35 cycles, followed by a final elongation step at 72° C. for 5 min.

After the amplification has occurred, aliquots of the reaction mixture are separated preferably by gel electrophoresis and the nucleic acids contained are made visible by staining. In more preferred embodiments, the gel electrophoresis is a poylacrylamide or agarose gel electrophoresis and/or the staining occurs using ethidium bromide and UV irradiation.

In a further aspect, the invention is directed to a washing buffer composed as detailed above. In a preferred embodiment, the washing buffer is a PBS buffer comprising at least 8%, and preferably 10%, BSA as well as at least one detergent.

In a preferred embodiment, the detergent is Tween 20 and/or Triton-X and is more preferably present in a concentration of 0.01 vol.-%.

In an especially preferred embodiment, the washing buffer further comprises potassium chloride 2.7 mM, potassium dihydrogen phosphate 1.5 mM, disodium hydrogen phosphate 8.1 mM, and/or sodium chloride 136.9 mM.

Also especially preferably the washing buffer is filled up with aqua dest. and adjusted to a pH value of 7.4 using HCl or NaOH.

In a further aspect, the present invention comprises the use of the washing buffer of the invention in a method of the invention.

In a further aspect, the invention is directed to a primer, which, like detailed above, is selected from the group consisting of a SEQ ID NO: 1, 2, 3, and 4. Furthermore, primers are encompassed by the invention comprising a sequence described in the SEQ ID NO: 1, 2, 3, or 4 and/or form a homologue to such a sequence. Preferably, such a homologue exhibits a nucleic acid identity of ≥80%, ≥85%, ≥90%, ≥91%, ≥92%, ≥93%, ≥94%, ≥95%, ≥96%, ≥97%, ≥98%, or ≥99%.

In a further aspect, the present invention comprises the use of the primers of the invention in one of the methods of the invention.

In a further aspect, the invention is directed to a kit comprising at least one type of beads of the invention coated with at least one antibody for at least one antigen, as well as the washing buffer of the invention comprising at least 8%, and preferably 10%, BSA.

In a preferred embodiment, the kit further comprises one, two, three, four, or five of the components according to the present invention selected from the group consisting of: positive control; negative control; reaction vessels; magnetic separator and operation manual.

In a further preferred embodiment, the kit further comprises one, two, three, or four of the components of the present invention selected from the group consisting of: secondary antibody (conjugate); HRP buffer; TMB substrate solution and stopping solution.

In a further preferred embodiment, the kit further comprises one, two, or three of the components of the present invention selected from the group consisting of: primer specific for an antigen, preferably a PCR primer pair; nucleic acid amplification buffer, preferably PCR reaction buffer and preferably separate from the nucleotide mix and the nucleic acid amplifying enzyme, preferably DNA polymerase; de-ionised water.

In a further aspect, comprises a device for performing the method of the present invention. Based on the explanations given above, the components of the device will reveal themselves easily to the skilled person. In particular, such a device comprises sample collection means, a photometric or colorimetric evaluation instrument and/or a thermocycler as well as an apparatus for gel electrophoresis.

The sample collection means can be any suitable means for delivering a suitable sample to the device. Exemplary sample collection means include syringes, pipettes, forceps, and suction devices, without limitation.

The photometric or colorimetric evaluation device can be for example any device for the reading of ELISA plates known to the skilled person. Likewise, the thermocycler and the gel electrophoresis apparatus can also be any suitable device known to the skilled person for performing a nucleic acid amplification or a gel electrophoresis, respectively.

In a preferred embodiment, the device is a mobile device. More preferably, the device is portable and/or movable on reels, wheels, or the like. This has the advantage that the method of the invention can be performed easily and quickly at nearly any location, without having to send the samples to a laboratory for analysis after collecting.

In a further preferred embodiment, the device is designed to perform the method of the invention semi- or fully automatically. Preferably an alert can be triggered on detection by the device of a certain antigen. This is advantageous especially for security applications, like e.g. at the airport, in which the continuous and automatic monitoring of certain substances, like e.g. biological weapons or drugs, is essential.

In a further aspect, the invention is directed to the use of the method, washing buffer, primers, kits, and device of the invention for the following applications:

Fast and sensitive detection of micro-organisms and other dangerous substances, particularly biological toxins. Fast detection of pathogens from body fluids, particularly blood, saliva, serum, tear fluid, and urine, in the field of medical diagnostics. Reliable detection of biohazardous materials for the identification and prevention of biological terrorist attacks. Prevention of epidemics and pandemics by a fast and reliable detection of infectious diseases (e.g. SARS) at the airport or other infrastructure. Fast detection of micro-organisms and hazardous substances in food monitoring. Protection of critical infrastructure (courthouses, agencies, federal facilities, etc.). Fast detection of micro-organisms on space missions and for finding extra-terrestrial life.

*Legionella* occur predominantly in hot water systems and ventilation systems. The danger of inhaling infectious aerosols is especially high in showers and whirlpools, particularly with low or irregular water extraction. By emission of infectious aerosols into the ambient air, ventilation systems can pose a source of infection that is not to be underestimated. Therefore, the detection of *Legionella* according to the invention in all standing and flowing water containers and/or ventilation systems is important for the protection of the following infrastructure (buildings and systems): ships of the navy, submarines, barracks, hospitals and/or field hospitals (e.g. during foreign missions), passenger airplanes (e.g. A380 with shower), retirement and nursing homes, hotels, hostels, medical and dentist practices, water suppliers of all kind, camping grounds, leisure facilities, particularly such with whirlpools, baths, fountains, condominiums, schools, kindergartens, passenger ships, penal institutions, swimming and sporting grounds, laboratory animal stalls, commercial real estate (production), one- and two-family homes (with and without air conditioning), condominiums (with and without air conditioning).

Adenoviruses, widespread worldwide, are extremely resistant against environmental influences and stable for weeks at room temperature. Therefore, small adenoviral epidemics can often occur in common facilities. Especially affected hereby are e.g. baths or barracks. For the containment of such epidemics, the fast and sensitive detection according to the invention is very important.

DETAILED DESCRIPTION OF THE INVENTION

EXAMPLES

Example 1

Production of the Antibody-Coated Beads

For the following detection experiments of antigens using the method of the invention, streptavidin beads and the following primary and secondary IgG antibodies or antibody pairs, respectively, have been used:

| Antibody | Organism | Company |
|---|---|---|
| anti-Adenovirus, biotin-conjugated | goat, polyclonal | Acris Antibodies |
| anti-Adenovirus, HRP-conjugated | goat, polyclonal | Acris Antibodies |
| anti-E. coli, biotin-conjugated | rabbit, polyclonal | Novus Biologicals |
| anti-E. coli, HRP-conjugated | rabbit, polyclonal | Novus Biologicals |
| anti-L. pneumophila | rabbit, polyclonal | Acris Antibodies |
| anti-L. pneumophila, biotin-conjugated | rabbit, polyclonal | Acris Antibodies |
| control antibodies employed: | | |
| anti-goat IgG, HRP-conjugated | rabbit, polyclonal | Abcam |
| anti-rabbit IgG, HRP-conjugated | goat | Novus Biologicals |

For producing the antibody-coated beads, the streptavidin beads were incubated with one of the biotin-conjugated antibodies, respectively.

Example 2

Optimisation of the Washing Buffer

A component of the washing buffer that is essential for the invention is the BSA present at a certain concentration. For determining the optimal concentration of BSA for the method of the invention, test series were conducted, wherein an unspecific binding of adenoviruses to the beads themselves was examined. For this, the beads were incubated overnight with different blocking reagents (0.1% BSA; 10% BSA; 5% milk powder, and 0.5 mg/ml biotin). In parallel, control experiments were performed to exclude that the blocking reagents employed inhibit the interaction between antigen and antibody. The beads were blocked with the washing buffer of different BSA concentrations and after incubation with the adenoviruses were washed with the same buffer before an adenovirus-specific PCR was performed.

Figure 1:
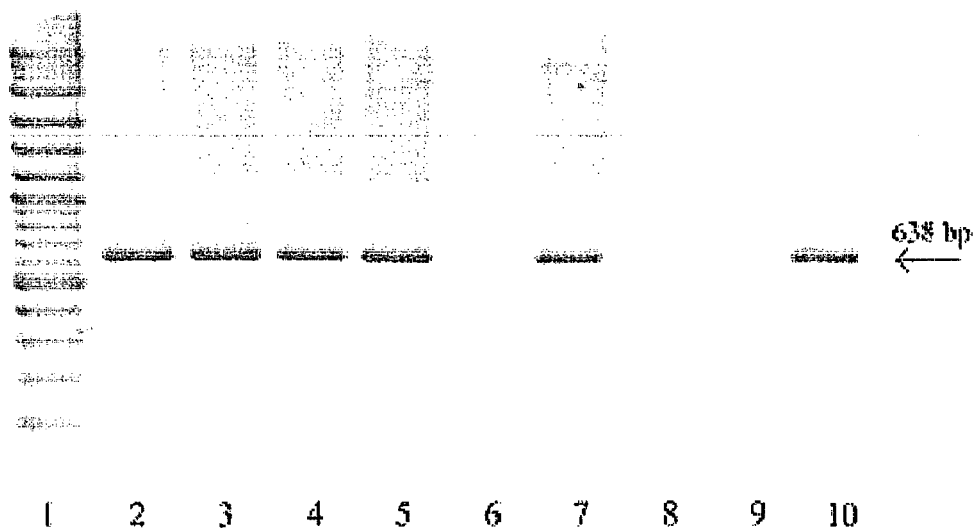
FIG. 1 shows the results of an experiment for blocking the unspecific binding sites of the beads.

FIG. 1 shows the results of this experiment of blocking unspecific binding sites of the beads with subsequent adenovirus-specific PCR. In particular, lane 1) shows DNA marker and lanes 2-5 positive controls, wherein lane 2) shows beads coated with adenovirus-specific antibodies, 0.1% BSA in the washing buffer, and incubation with adenoviruses, lane 3) shows beads coated with adenovirus-specific antibodies, 10% BSA in the washing buffer, and incubation with adenoviruses, lane 4) shows beads coated with adenovirus-specific antibodies, 5% milk powder in the washing buffer, and incubation with adenoviruses, lane 5) shows beads coated with adenovirus-specific antibodies, 0.5 mg/ml biotin in the washing buffer, and incubation with adenoviruses. Lane 6) is empty.

The results of the blocking assays can be seen in lanes 7-10, wherein lane 7) shows uncoated beads with 0.1% BSA in the washing buffer and incubation with adenoviruses; lane 8) shows beads with 10% BSA in the washing buffer and incubation with adenoviruses; lane 9) shows beads with 5% milk powder in the washing buffer and incubation with adenoviruses; lane 10) shows beads with 0.5 mg/ml biotin in the washing buffer and incubation with adenoviruses.

As a result, it can clearly be seen that with insufficient blocking, adenoviruses bind to beads unspecifically and the corresponding genome section is amplified in the subsequent PCR (lanes 7 and 10). With sufficient blocking, the adenoviruses are not bound unspecifically and no amplification takes place.

The experiment has been repeated with *Legionella* and with comparable experimental results.

Taken together, it could be shown that with a lower concentration of BSA (e.g. 0.1%), the antigen (*Legionella* or Adenoviruses) binds unspecifically to the magnetic beads and the desired specific antigen-antibody reaction of the invention does not occur.

It could be shown experimentally that blocking (saturating unused binding sites on the beads) before and during the washing can massively prevent an unspecific interaction. The blocking of the beads with 10% BSA overnight yielded the best results. A blocking of the beads with 8% BSA also yielded very good results. For this reason, BSA in a range of 3-12% was added to the washing buffer (PBS).

Example 3

Immunological Detection

The method of the invention was performed with subsequent immunological detection.

For this, the antibody pairs listed above were used, as well as the following solutions:

PBS Washing Buffer:

| | Amount | Final concentration |
|---|---|---|
| Potassium chloride | 0.2 g | 2.7 mM |
| Potassium dihydrogen phosphate | 0.2 g | 1.5 mM |
| Disodium hydrogen phosphate | 1.15 g | 8.1 mM |
| Sodium chloride | 8.0 g | 136.9 mM |
| BSA, biotin-free | 100 g | 8% |
| Tween 20 | 0.1 ml | 0.01% |
| Aqua dest. | ad 1000 ml | | pH 7.4 adjusted with hydrochloric acid or sodium hydroxide.

Conjugate Solution

The conjugated antibody was diluted in PBS 1:750.

HRP Buffer

| | | |
|---|---|---|
| Potassium citrate | 6.9 g | 30 mM |
| Aqua dest. | ad 1000 ml | |

Adjust to pH 4.1 with potassium hydroxide

TMB Substrate Solution

| | | |
|---|---|---|
| Tetramethylbenzidine | 240 mg | 10 mM |
| Acetone (96%) | 10 ml | |
| Ethanol (96%) | 90 ml | |
| Hydrogen peroxide (30%) | 750 µl | |

Stopping Solution

| 96% sulphuric acid | 6 ml | 1M |
| Aqua dest. | ad 95 ml | |

Figure 2:
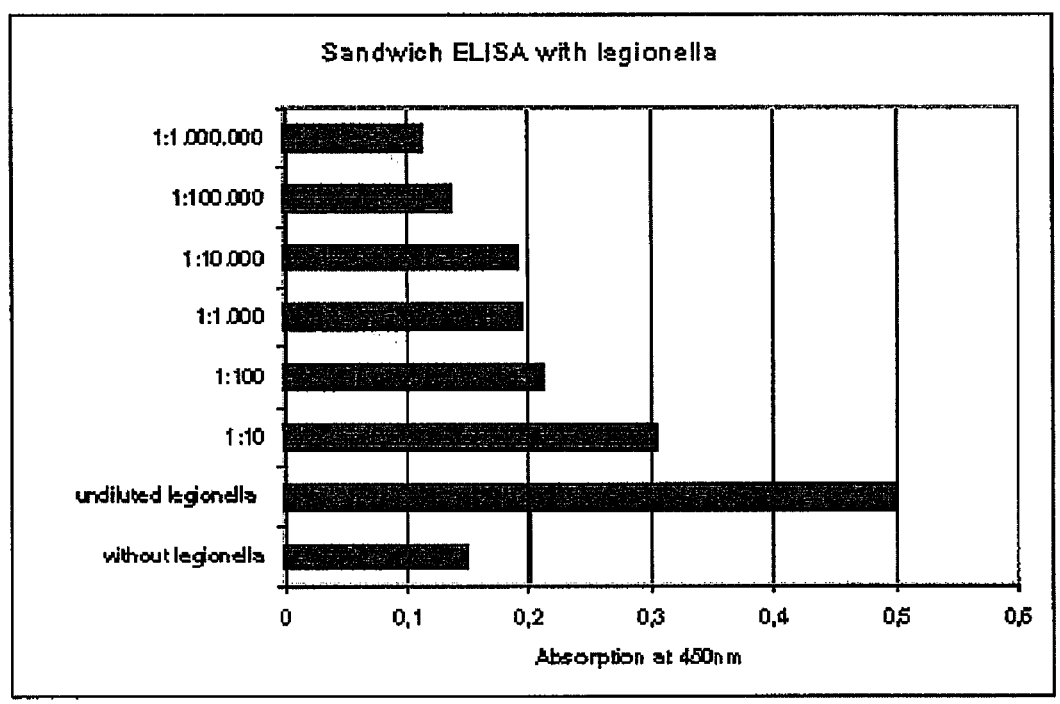
FIG. 2 shows the detection of *Legionella pneumophila* by means of an immunological method according to the invention.

The method was performed according to the following schedule:
1) Withdrawal of 8 µl of antibody-coated beads (7-12×10$^8$ beads/ml) and transfer into the reaction tube
2) 5× washing of the beads on the magnetic separator with 400 µl PBS at a time
3) Uptake into 8 µl PBS
4) Addition of 36 µl sample
5) Incubation of 1 h at room temperature, stirring of the sample every 15 min
6) 5× washing of the beads on the magnetic separator with 400 µl PBS at a time
7) Uptake into 200 µl conjugate solution
8) Incubation of 1 h at room temperature, stirring of the sample every 15 min
9) 5× washing of the beads on the magnetic separator with 400 µl PBS at a time
10) Uptake of the beads into 20 µl PBS
11) Pipetting 1000 µl HRP buffer+50 µl TMB substrate solution into a reaction tube and addition of the 20 µl beads from step 10
12) Stirring of the sample
13) Incubation of 45 min at room temperature
14) Stopping of the reaction with 500 µl stopping solution
15) Stirring of the sample
16) Incubation of 10 min at room temperature
17) Evaluation of the assay using the evaluation instrument FIG. 2 shows the results of the detection of *Legionella pneumophila*, wherein different *Legionella* dilutions were detected using the method described above. The detection limit lay at a dilution of 1:10,000, corresponding to a total cell number of 7,416 *Legionella*.

Figure 3:
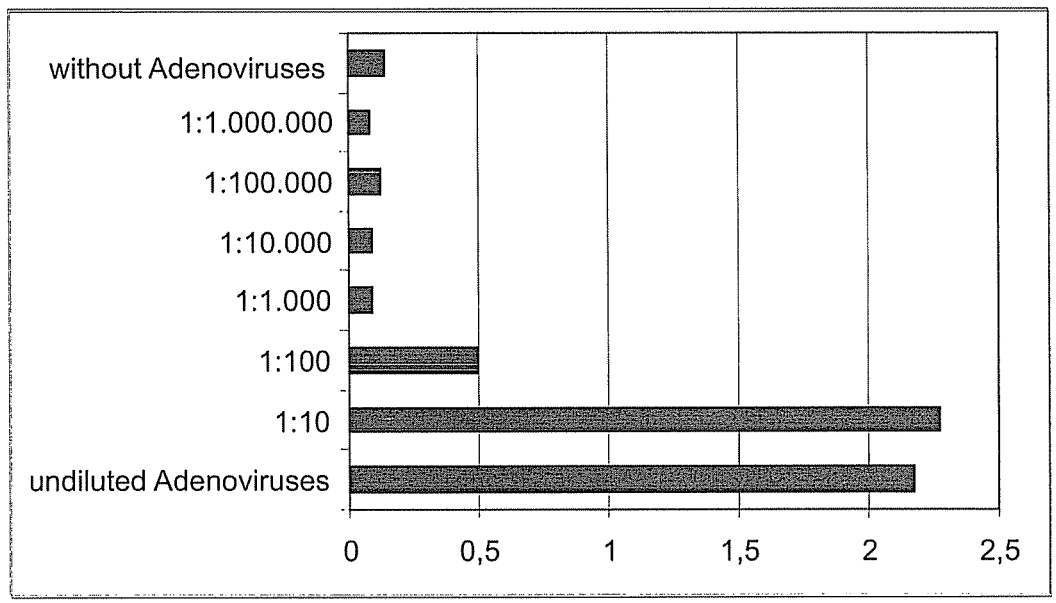
FIG. 3 shows the detection of adenovirus by means of an immunological method according to the invention.

FIG. 3 shows the results of the detection of Adenovirus (subgroup C, serotype 6), wherein the adenoviruses were diluted by means of a dilution series and incubated with the beads coated with specific antibodies. The actual detection occurred subsequently also via the conjugate using the enzymatic reaction of the "horseradish peroxidise" (HRP). Adenoviruses could be specifically detected down to a dilution of 1:100.

Figure 4:
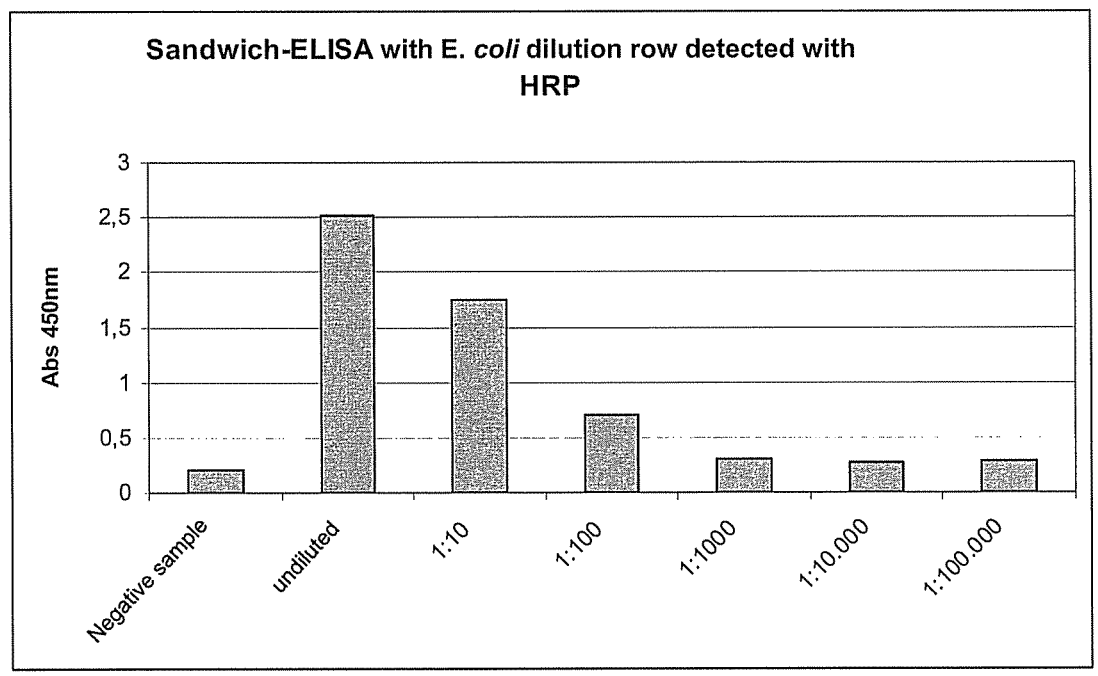
FIG. 4 shows the detection of *E. coli* by means of an immunological method according to the invention.

FIG. 4 shows the results of the detection of *E. coli*, wherein the bacteria were diluted in steps of 10 and incubated with magnetic beads, respectively. After stringent washing, the bacteria were also detected colorimetrically with TMB as substrate. *E. coli* could be detected down to a dilution of 1:100, corresponding to a total cell number of 6,000 bacteria (after cultivation of the bacteria on Petri dishes, a cell number of 6,000 organisms could be determined for the 1:100 dilution).

Example 4

Detection Using Nucleic Acid Amplification (PCR)

Besides the immunological detection of *Legionella pneumophila* and Adenovirus, molecular biological assays using the PCR methods were also developed. The method of the invention was thus performed with subsequent detection via PCR.

For this, the antibodies mentioned above were used for the production of the coated beads, as well as the following solutions:

PBS Washing Buffer:

| | Amount | Final concentration |
|---|---|---|
| Potassium chloride | 0.2 g | 2.7 mM |
| Potassium dihydrogen phosphate | 0.2 g | 1.5 mM |
| Disodium hydrogen phosphate | 1.15 g | 8.1 mM |
| Sodium chloride | 8.0 g | 136.9 mM |
| BSA, biotin-free | 100 g | 10% |
| Tween 20 | 0.1 ml | 0.01% |
| Aqua dest. | ad 1000 ml | | pH 7.4 adjusted with hydrochloric acid or sodium hydroxide.

PCR Reaction Buffer with $MgCl_2$
  10 mM Tris-HCl (pH 8.3),
  50 mM KCl
  1.5 mM $MgCl_2$
Nucleotide Mix
  A final concentration of 200 µM nucleotide mix was used per assay. The stock solution amounted to 10 mM.
Taq DNA Polymerase
  0.02 units/µl Taq DNA polymerase were used per assay.
  The following primer pairs were used for the specific detection of *Legionella pneumophila* and Adenovirus:

| | Primer sequence |
|---|---|
| Legionella pneumophila: | |
| ompS_Leg_forward | 5'-GCG GCT GTA TTT GCT CTG GGA A-3' |
| ompS_Leg_reverse | 5'-TAA GCC TAT GTA GGG GCC AGA TGC-3' |
| Adenovirus: | |
| hexon_AdV_forward | 5'-GAA ATG ACA CCA ACG ACC AG-3' |
| hexon_AdV_reverse | 5'-GGG AAC ATT AGC GGG GTA AG-3' |

100 pmol per primer were used per assay.

These primer pairs are specific for certain marker genes in *Legionella* and Adenovirus.

The detection of *Legionella pneumophila* was respectively performed with specific primers for the gene ompS, encoding a highly conservative membrane protein. The primers of this primer pair lie at positions 294-315 and 1119-1142 of the DNA sequence of the ompS protein of *L. pneumophila*, which is known to the skilled person (Gene Bank accession number: M76178.1).

The detection of Adenovirus was respectively performed with specific primers for the capsid gene hexon. Here the primer pair was designed based on conserved regions. The primers of this primer pair lie at positions 1937-1956 and 2555-2574 of the DNA sequence of the hexon protein of adenoviruses, which is known to the skilled person (Gene Bank accession number: AB330087.1).

For the amplification of DNA fragments of both microorganisms, one corresponding primer pair, of those listed above was used, respectively. The amplification occurred in several cycles with three reaction steps each. In the first reaction step, the DNA double strand was melted into single strands by heating to 95° C., which the complementary oligonucleotides annealed to upon quick chilling. In the third reaction step, starting from the primers, double strands were synthesised in the presence of the nucleotides (dNTPs), while the temperature was increased to 72° C., the optimal reaction temperature of the polymerase.

The amplification occurred under the following conditions:

| | | |
|---|---|---|
| 1) Denaturing: | 95° C./5 min | |
| 2) Denaturing: | 95° C./20 s | |
| 3) Annealing of the primers: | 20 s | 30-35 cycles |
| For *Legionella pneumophila*: | at 58° C. | |
| For Adenovirus: | at 54° C. | |
| 4) Elongation: | 72° C./1 min | |
| 5) Elongation: | 72° C./5 min | |

At the beginning of the amplification round, the matrix DNA was heated for 5 min to 95° C. in order to denature it completely. Afterwards, the amplification of the DNA fragment occurred in 30-35 cycles. As annealing temperature, the value of the primer having the lower melting temperature was used. The polymerisation time was chosen between 20 s and 3 min, depending on the length of the fragment to be amplified. A polymerisation period of 1 min per 1 kb was assumed. After the last polymerisation step at 72° C., this temperature was maintained for further 5 min in order to ensure complete polymerisation. 50 μl mixtures in 0.5 ml reaction tubes were prepared.

Experimental Results for *Legionella pneumophila*

Experiments for the qualitative and quantitative detection using the marker gene ompS were performed. For the detection of *Legionella pneumophila* via PCR, 5 μl beads were used, respectively, to which *Legionella* from a dilution series had previously been bound. The detection occurred with specific ompS primers, respectively. Beads without template, beads+PBS, and beads with a foreign antigen were used as negative controls, respectively.

Figure 5:
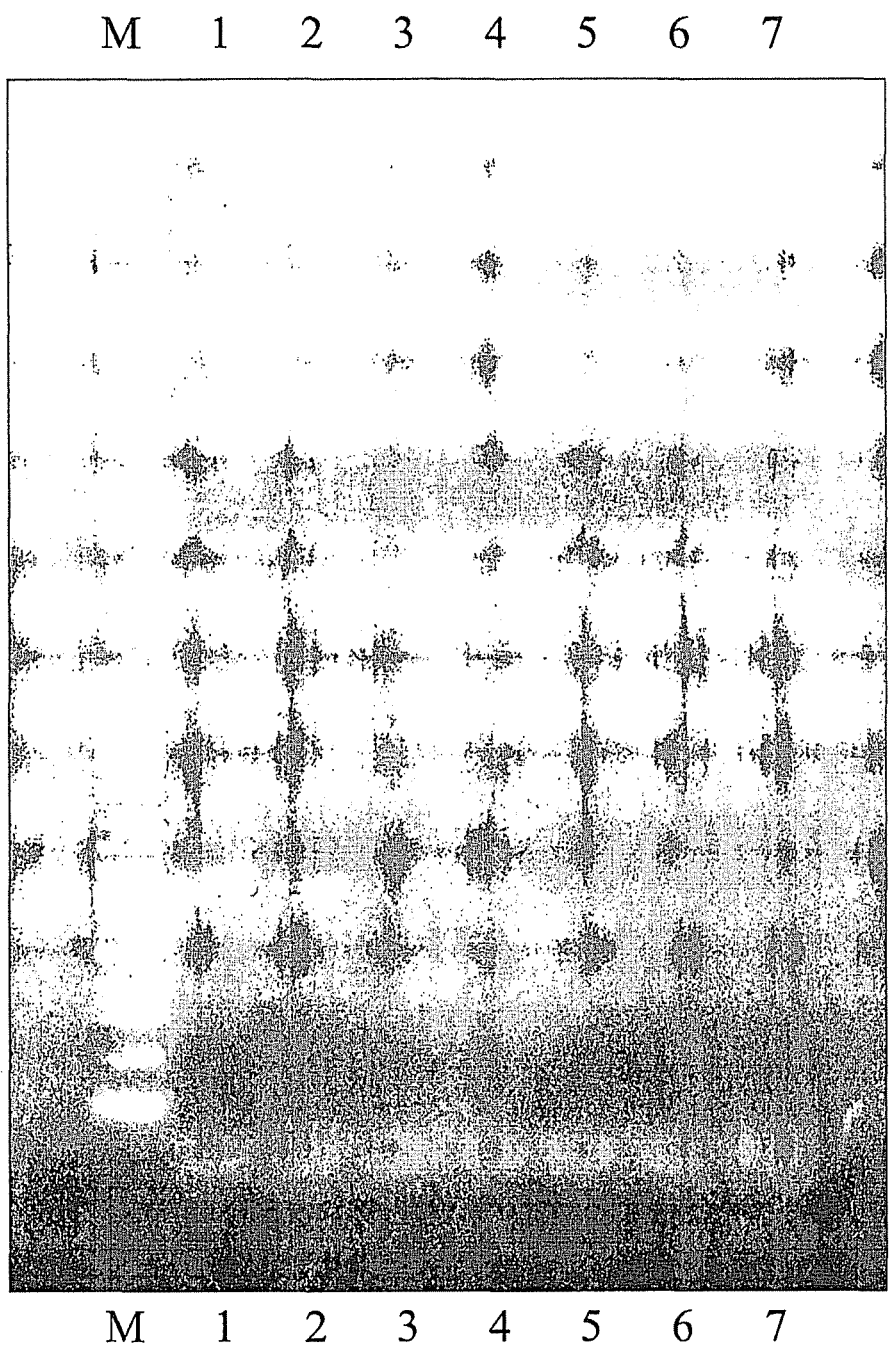
FIG. 5 shows the qualitative and quantitative detection of *Legionella pneumophila* by means of a nucleic acid amplification method according to the invention.

As can be recognised in FIG. 5, it could be shown that only beads with bound *Legionella* as template yielded a signal (qualitative detection). For the quantification, a PCR on genomic *Legionella* DNA was performed simultaneously. For this, a defined amount of genome copies ($2 \times 10^6$) was diluted in a dilution series and employed in the PCR. After electrophoretic separation of the amplificates the detection limit could be estimated by means of the agarose gel (quantitative detection).

FIG. 5 shows the qualitative and quantitative detection of *Legionella pneumophila*.

On the upper agarose gel, a dilution series starting from a defined genome copy concentration can be seen: lane 1) $2 \times 10^6$ genomes, lane 2) $2 \times 10^5$ genomes, lane 3) $2 \times 10^4$ genomes, lane 4) $2 \times 10^3$ genomes, lane 5) $2 \times 10^2$ genomes, lane 6) $2 \times 10^1$ genomes, lane 7) negative control without genome copies.

On the lower agarose gel, a dilution series of *Legionella pneumophila* can be seen: lane 8) detection of about $2 \times 10^3$ *Legionella* bound to magnetic beads, lane 9) detection of about $2 \times 10^1$ *Legionella* bound to magnetic beads, lane 10) detection of about $2 \times 10^2$ *Legionella* bound to magnetic beads, lane 11) detection of about $2 \times 10^0$ *Legionella* bound to magnetic beads, lane 12) negative control without *Legionella* bound to magnetic beads, lane 13) PCR with washing buffer (PBS), lane 14) PCR with foreign antigen, lane M) DNA marker a band corresponds to 100 base pairs.

As can further be derived from FIG. 5, the detection limit lies at a concentration of 2,000 to 200 cells/12 μl.

Experimental Results for Adenoviruses

For the detection of Adenoviruses, the above-mentioned primers for the marker gene hexon were used. It could be shown that results comparable to the *Legionella* can be achieved with these primers.

The invention claimed is:

1. A method for the detection of at least one antigen in a sample comprising the steps of:
   (a) coating magnetic beads with at least one antibody specific for the at least one antigen;
   (b) washing the coated beads with a first washing solution comprising a buffer and about 8% to 12% bovine serum albumin (BSA);
   (c) incubating the washed beads with the sample to form a mixture;
   (d) washing the mixture with a second washing solution comprising a buffer;
   (e) isolating the beads using a magnetic separator; and
   (f) detecting the at least one antigen in the sample.

2. The method of claim 1 wherein the first washing solution further comprises a detergent.

3. The method of claim 1 wherein the second washing solution further comprises about 8% to 12% BSA.

4. The method of claim 1 wherein the first washing solution and the second washing solution are the same.

5. The method of claim 1 wherein the washing step (b) is performed by incubating the coated beads in the first washing solution for at least 30 minutes to 12 hours.

6. The method of claim 1 wherein detecting the at least one antigen is performed using a nucleic acid amplification method.

7. The method of claim 1 wherein detecting the at least one antigen is performed using an enzyme-linked immunosorbent assay (ELISA) assay.

8. The method of claim 1 where the washing step (b) is repeated at least one time prior to the incubation step (c).

9. The method of claim 1 wherein the washing step (d) is repeated at least one time after the incubation step (c).

10. The method of claim 1 wherein the washing step (d) occurs on a magnetic separator.

11. The method of claim 1 where the at least one antigen to be detected is from a microorganism selected from the group consisting of a bacterium, a virus, a fungus, a toxin, LPS, and protozoa.

12. The method of claim 1 where the at least one antibody comprises an antibody specific for a microorganism selected from the group consisting of a bacterium, a virus, a protozoon, a fungus; and an antibody specific for a toxin produced by the microorganism, the bacterium, the virus, the protozoon, and the fungus.

13. The method of claim 11 wherein the microorganism is selected from *Escherichia coli*, adenovirus, and *Legionella* spp.

14. The method of claim 12 wherein the microorganism is selected from *Escherichia coli*, adenovirus, and *Legionella* spp.

* * * * *

SEQUENCE LISTING

<160> NUMBER OF SEQ ID NOS: 4

<210> SEQ ID NO 1
<211> LENGTH: 22
<212> TYPE: DNA
<213> ORGANISM: Artificial
<220> FEATURE:
<223> OTHER INFORMATION: Forward Primer for the Legionella pneumophila
      ompS Gene

<400> SEQUENCE: 1
gcggctgtat ttgctctggg aa                                            22

<210> SEQ ID NO 2
<211> LENGTH: 24
<212> TYPE: DNA
<213> ORGANISM: Artificial
<220> FEATURE:
<223> OTHER INFORMATION: Reverse Primer for the Legionella pneumophila
      ompS Gene

<400> SEQUENCE: 2

-continued

```
taagcctatg taggggccag atgc                                      24

<210> SEQ ID NO 3
<211> LENGTH: 20
<212> TYPE: DNA
<213> ORGANISM: Artificial
<220> FEATURE:
<223> OTHER INFORMATION: Forward Primer for the adenoviral Hexon-Gene

<400> SEQUENCE: 3
gaaatgacac caacgaccag                                           20

<210> SEQ ID NO 4
<211> LENGTH: 20
<212> TYPE: DNA
<213> ORGANISM: Artificial
<220> FEATURE:
<223> OTHER INFORMATION: Reverse Primer for the adenovirale Hexon Gene

<400> SEQUENCE: 4
gggaacatta gcggggtaag                                           20
```